(12) United States Patent
Krammer et al.

(10) Patent No.: US 9,675,568 B2
(45) Date of Patent: Jun. 13, 2017

(54) PHARMACEUTICAL COMPOSITIONS

(71) Applicant: Symrise AG, Holzminden (DE)

(72) Inventors: Gerhard Krammer, Holzminden (DE); Sven Siegel, Höxter (DE); Silke Middendorf, Bad Laer (DE)

(73) Assignee: Symrise AG, Holzminden (DE)

( * ) Notice: Subject to any disclaimer, the term of this patent is extended or adjusted under 35 U.S.C. 154(b) by 97 days.

(21) Appl. No.: 14/075,406

(22) Filed: Nov. 8, 2013

(65) Prior Publication Data
US 2014/0134113 A1    May 15, 2014

(30) Foreign Application Priority Data

Nov. 8, 2012 (EP) .................................... 12191877

(51) Int. Cl.
| | | |
|---|---|---|
| *A61K 31/167* | (2006.01) | |
| *A61K 45/06* | (2006.01) | |
| *A61K 9/00* | (2006.01) | |
| *A61K 9/68* | (2006.01) | |
| *A61Q 11/00* | (2006.01) | |
| *A61K 31/196* | (2006.01) | |
| *A61K 8/42* | (2006.01) | |

(52) U.S. Cl.
CPC .............. *A61K 31/167* (2013.01); *A61K 8/42* (2013.01); *A61K 9/006* (2013.01); *A61K 9/0056* (2013.01); *A61K 9/0058* (2013.01); *A61K 9/0063* (2013.01); *A61K 9/0095* (2013.01); *A61K 31/196* (2013.01); *A61K 45/06* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 4,136,163 A | 1/1979 | Watson et al. | |
| 2007/0178123 A1* | 8/2007 | Levenson | A61K 9/0053 424/400 |
| 2010/0086498 A1* | 4/2010 | Haught | A61K 8/19 424/49 |
| 2011/0195042 A1* | 8/2011 | Huetter | A61K 9/006 424/78.32 |

FOREIGN PATENT DOCUMENTS

| | | |
|---|---|---|
| EP | 2186506 A1 | 5/2010 |
| JP | 2012152127 A | 8/2012 |
| WO | 2005002582 A2 | 1/2005 |
| WO | 2008015403 A1 | 2/2008 |
| WO | WO 2008015403 A1 * | 2/2008 ........... A61K 36/534 |

OTHER PUBLICATIONS

McKemy, D.D. Therapeutic Potential of TRPM8 modulator. The Open Drug Discovery Journal, 2010, 2, 81-88.*
Ladonna C . Wood, Peter M. Elias, Cornelia Calhoun, Janice C. Tsai, Carl Grunfeld, and Kenneth R. Feingold. Barrier Disruption Stimulates Interleukin-1a Expression and Release from a Pre-Formed Pool Murine Epidermis. J. Invesest Dermatol 106:397-403, 1996.*
Mitsuhiro Denda, Moe Tsutsumi and Sumiko Denda. Topical application of TRPM8 agonists accelerates skin permeability barrier recovery and reduces epidermal proliferation induced by barrier insult: role of coldsensitive TRP receptors in epidermal permeability barrier homoeostasis. Experimental Dermatology 2010, 19, 791-795.*
Ron Eccles. Understanding the symptoms of the common cold and influenza. Lancet Infect Dis 2005; 5: 718-725.*
Sherkheli MA, Gisselmann G, Vogt-Eisele AK, Doerner JF and Hatt H. Menthol Derivative WS-12 Selectively Activates Transient Receptor Potential Melastatin-8 (TRPM8) Ion Channels. Pak. J. Phann. Sci., vol. 21, No. 4, Oct. 2008, pp. 370-378.*

* cited by examiner

*Primary Examiner* — Frederick Krass
*Assistant Examiner* — Michael P Cohen
(74) *Attorney, Agent, or Firm* — Dilworth & Barrese, LLP

(57) ABSTRACT

Suggested is a pharmaceutical composition, comprising menthane carboxylic acid-N-(4-methoxy-phenyl)-amide.

8 Claims, No Drawings

PHARMACEUTICAL COMPOSITIONS

FIELD OF INVENTION

The present invention belongs to the area of anti-inflammatory compositions and refers to a specific menthane carboxylic acid amide as a pharmaceutical composition and also oral compositions comprising said amide.

STATE OF THE ART

Inflammation represents a part of the complex biological response of vascular tissues to harmful stimuli, such as pathogens, damaged cells, or irritants. An inflammation is different to a mere irritation like goose bumps or itching in the case of the skin. Inflammation is a protective attempt by the organism to remove the injurious stimuli and to initiate the healing process. Inflammation is not a synonym for infection, even in cases where inflammation is caused by infection. Although infection is caused by a microorganism, inflammation is one of the responses of the organism to the pathogen. However, inflammation is a stereotyped response, and therefore it is considered as a mechanism of innate immunity, as compared to adaptive immunity, which is specific for each pathogen. An acute inflammation is preferably characterized by clinical signs: pain, redness, immobility (loss of function), swelling and/or heat. A very typical embodiment of inflammation is acne vulgaris.

The process of acute inflammation is initiated by cells already present in all tissues. These cells have on their surfaces certain pattern recognition receptors (PRRs), which recognize molecules that are broadly shared by pathogens but distinguishable from host molecules (pathogen-associated molecular patterns (PAMPs)). At the onset of an infection, burn, or other injuries, these cells undergo activation (as one of their PRRs recognizes a PAMP) and release inflammatory mediators (factors) responsible for the clinical signs of inflammation. Vasodilation and its resulting increased blood flow cause the redness (rubor) and increased heat (calor). Increased permeability of the blood vessels results in an exudation (leakage) of plasma proteins and fluid into the tissue (edema), which manifests as swelling (tumor). Some of the released mediators increase the sensitivity to pain (dolor). The mediator molecules also alter the blood vessels to permit the migration of leukocytes, mainly neutrophils, outside of the blood vessels (extravasation) into the tissue. The neutrophils migrate along a chemotactic gradient created by the local cells to reach the site of injury. The loss of function (functio laesa) is probably the result of a neurological reflex in response to pain. Preferably, in the sense of this text, an inflammation is accompanied by an elevated level of inflammatory mediators (factors) like TNF-α (Tumor necrosis factor-alpha), interleukins, (preferably of IL-1, IL-6, IL-7, IL-8, IL-10, IL-13, IL-17, IL-18 and/or IL-31, in particular IL-1), prostaglandin (preferably $PGI_2$, $PGE_2$ and/or $PGF_{2\alpha}$), Interferon-gamma (INF-γ) and/or NF-κB (nuclear factor kappa-light-chain-enhancer of activated B cells).

Among the various types of inflammatories inflammation of the respiratory tract is one of the most common, particular in winter time. The respiratory tract is divided into three segments: the upper respiratory tract, which includes the nose and nasal passages, paranasal sinuses, and throat or pharynx; the respiratory airways, which include the voice box or larynx, trachea, bronchi, and bronchioles; and the lungs, which include the respiratory bronchioles, alveolar ducts, alveolar sacs, and alveoli. The term upper respiratory infections, commonly referred to as URIs, are used to refer to an acute infection that involves the upper respiratory tract, e.g., the nose, sinuses, pharynx or larynx. Acute upper respiratory tract infections include rhinosinusitis (common cold), sinusitis, pharyngitis/tonsillitis, laryngitis and sometimes bronchitis. Symptoms of URIs commonly include congestion, cough, running nose, sore throat, fever, facial pressure and sneezing. These infections very often have inflammation as a symptom. An also very common infection is pharyngitis. Pharyngitis is, in most cases, a painful inflammation of the pharynx, and is colloquially referred to as a sore throat. Infection of the tonsils, i.e., tonsillitis, may occur simultaneously. About 90% of cases are caused by viral infection, with the remainder caused by bacterial infection and, in rare cases, oral thrush (fungal candidiasis, e.g., in babies). Some cases of pharyngitis are caused by irritation from environmental irritants such as pollutants or chemical substances As a matter of fact countless actives are known from the state of the art. For example, U.S. Pat. No. 4,136,163 describe compounds having a physiological cooling effect on the skin and on the mucous membranes of the body, particularly those of the mouth, nose, throat and gastrointestinal tract. These compounds are 3-substituted-p-menthanes of formula (I):

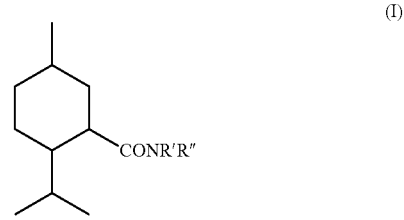

Where R', when taken separately, is hydrogen or an aliphatic radical containing up to 25 carbon atoms; R", when taken separately is hydroxy, or an aliphatic radical containing up to 25 carbon atoms, with the proviso that when R' is hydrogen R" may also be an aryl radical of up to 10 carbon atoms and selected from the group consisting of substituted phenyl, phenalkyl or substituted phenalkyl, naphthyl and substituted naphthyl, pyridyl (with typical values being benzyl, naphthyl, 4-methoxyphenyl, 4-hydroxyphenyl, 4-methylphenyl, 3-hydroxy-4-methylphenyl, 4-fluorophenyl, 4-nitrophenyl, 2-hydroxynaphthyl, pyridyl, etc.); and R' and R", when taken together with the nitrogen atom to which they are attached, represent a cyclic or heterocyclic group of up to 25 carbon atom.

U.S. Pat. No. 4,136,163 teaches that the compounds of formula (I) are suitable for a wide variety of applications including edible and potable compositions, toiletries, medicaments including counterirritants, cough mixtures and throat lozenges as well as miscellaneous compositions such as water soluble adhesive compositions for envelopes, stamps, adhesive labels etc. Regarding medicaments, U.S. Pat. No. 4,136,163 teaches that because of their cooling effect on the skin and on the mucous membranes of the mouth, throat and nose and of the gastrointestinal tract the 3-substituted-p-menthanes may be used in a variety of oral medicines, nasal and throat sprays, and topical compositions. A particular utility is in the formulation of antacid and indigestion remedies. An anti-inflammatory effect of the compounds of formula (I) is not disclosed.

More than fifty compounds of formula (I) are specifically mentioned in U.S. Pat. No. 4,136,163. Although menthane carboxylic acid-N-(4-methoxyphenyl)-amide is one of the compounds explicitly mentioned, no example of a composition comprising said compound is provided. Indeed, none of the twenty-four given composition examples comprises any compound of formula (I) wherein R' is hydrogen and R" is an aryl radical of up to 10 carbon atoms as defined above.

WO 2009 021558 A1 relates to products and mixtures comprising (a) pellitorin and (b) selected cooling agents different from menthane carboxylic acid-N-(4-methoxyphenyl)-amide, and the use of such mixtures for soothing irritated oral and/or nasal tissues and for reducing bitterness. The mixture optionally comprises one or more additional physiological cooling agents selected from the group consisting of N-substituted-p-menthane-3-carboxamides (as described in U.S. Pat. No. 4,136,163), acyclic tertiary and secondary carboxamides, 3-(1-menthoxy)propan-1,2-diol, monomenthyl glutarate, monomenthyl succinate and its salts. The sole specific example of an N-substituted-p-menthane-3-carboxamide given in the document is ethyl-p-menthane-3-carboxamide. An anti-inflammatory effect of N-substituted-p-menthane-3-carboxamides is not disclosed.

U.S. Pat. No. 6,231,900 B1 discloses a pastille confectionery product, suitable for the relief of cough and cold symptoms, comprising a coolant composition and a flavour composition each composition being in separate, distinct and discrete regions of the product, the coolant and flavour compositions being adapted to provide different release profiles; wherein the coolant composition is free of flavouring agents and the flavour composition is essentially free of cooling agents. Anti-irritant or anti-inflammatory effects are not mentioned.

US 2009/0238905 A1 relates to a composition for reducing inflammation and irritation of endodermal tissue, such as that in the gastrointestinal tract and the respiratory tract. The formulation comprises an ingestible carrier or coating and an active mixture that includes bisabolol or extracts containing bisabolol and a ginger composition. The composition advantageously comprises one or more cooling agents, among others the above-mentioned menthyl-3-carboxylic acid N-ethylamide. No further cooling agents of formula (I) are mentioned in US 2009/0238905. The ratio of bisabolol to the ginger composition in the active mixture is such that an irritation reducing action, an inflammation reducing action, or both, of the bisabolol and the ginger composition is increased synergistically. The composition may comprise further anti-inflammatories selected from corticosteroid-type steroidal actives, non-steroidal active, and combinations thereof; and natural anti-inflammatory substances. Thus, the anti-irritating and anti-inflammatory action of the compositions is the result of the presence of ginger and bisabolol and (if present) one or more further conventional anti-inflammatories.

WO 2007 021603 A1 describes a composition for modulating oral and/or nasal secretion comprising a salivating agent and a cooling agent comprising menthol, peppermint oil, N-substituted-p-menthane-3-carboxamides (as described in described in U.S. Pat. No. 4,136,163), acyclic tertiary and secondary carboxamides, 3-1-menthoxy propan-1,2-diol, monomenthyl glutarate and mixtures thereof. The sole specific example of an N-substituted-p-menthane-3-carboxamide given in this document is ethyl-p-menthane-3-carboxamide. An anti-inflammatory effect of N-substituted-p-menthane-3-carboxamides is not disclosed.

WO 2008 015403 A1 discloses the use of a transient receptor potential (TRP) M8 cation channel activating agent in the manufacture of a medicament for the induction of analgesia in a patient suffering from or experiencing chronic neuropathic pain, wherein the TRPM8 activating agent is the menthyl derivative compound 2-isopropyl-5-methyl-cyclohexane-carboxylic acid 4-methoxyphenyl amide (WS12). The list of chronic neuropathic pains includes inflammatory pain states. Thus, while this medicament is useful in treating pain as a symptom of an inflammation, it is not disclosed to be effective against the inflammation as such which is the cause of the pain. In a nut shell, so far none of the actives known from the state of the art have been found to satisfy the needs of the consumers. Those showing a high performance also exhibit severe negative side-effects, those which were founds to be safe, do not show either sufficient activity or limited with respect to the various reason that lead to inflammation. Thus, there is an on-going need for substances having an anti-inflammatory effect, in particular for the treatment of, coughs, colds, oral, nasal, throat or pharyngeal inflammation, sore throat, hoarseness and other inflammations of the respiratory tract. Therefore the problem underlying the present invention has been identifying a new active that simultaneously fulfils the following complex profile:

toxicologically safe,
well tolerated by the skin,
stabile (in particular in pharmaceutical formulations),
low odour or (as far as possible) odourless,
colourless and not discolouring, and
economical to produce (i.e. by using standard methods and/or on the basis of standard precursors).

In this context it should be noted, that the search for anti-inflammatories having one or more of the said characteristics to a sufficient degree, is made harder for a person skilled in the art by the fact that there is not clear dependency between the chemical structure of a substance on the one hand and its anti-inflammatory activity and its stability on the other. Furthermore, there is no predictable correlation between the anti-inflammatory effect, the toxicological safety, the tolerance by the skin and/or the stability.

DESCRIPTION OF THE INVENTION

A first object of the present invention is directed to a pharmaceutical composition comprising menthane carboxylic acid-N-(4-methoxy-phenyl)-amide.

Additional objects of the present invention concern a pharmaceutical composition comprising menthane carboxylic acid-N-(4-methoxy-phenyl)-amide for:

Treating and/or preventing skin inflammation.
Reducing the release of TNF-α (Tumor necrosis factor-alpha).
Reducing the release of an interleukin.
Reducing the release of a prostaglandin.
Reducing the release of interferon-gamma (INF-γ) and/or NF-κB (nuclear factor kappa-light-chain-enhancer of activated B cells).

Surprisingly, it has been observed that menthane carboxylic acid-N-(4-methoxyphenyl)-amide has a powerful anti-inflammatory effect and fulfills the complex profile explained above.

Menthane carboxylic acid-N-(4-methoxy-phenyl)-amide

The compound menthane carboxylic acid-N-(4-methoxyphenyl)-amide comprises two enatiomers, namely L-menthane carboxylic acid-N-(4-methoxyphenyl)-amide and D-menthane carboxylic acid-N-(4-methoxyphenyl)-amide. It has been found that the anti-inflammatory effect of the L-enantiomer is significantly more pronounced than that of the D-enantiomer. For this reason, the menthane carboxylic acid-N-(4-methoxyphenyl)-amide for use as a medicament according to the present invention is preferably L-menthane carboxylic acid-N-(4-methoxyphenyl)amide. Accordingly, the component (A) of the mixture according to the invention preferably comprises, essentially consists of or consists of L-menthane carboxylic acid-N-(4-methoxyphenyl)-amide.

The active is known in the art and has widely been used as a cooling agent. Another conventional application of menthane carboxylic acid-N-(4-methoxyphenyl)-amide exploits the capability of that compound to mask the bitterness of menthol. EP 2 186 506 discloses teeth-cleaning composition comprising a cleaning agent and a flavoring composition, which consists of menthol, menthane carboxylic acid-N-(4-methoxyphenyl)-amide in an amount to mask the bitterness of menthol and at least one further flavoring agent Based on these conventional fields of application of menthane carboxylic acid-N-(4-methoxyphenyl)-amide the skilled person would not reasonably have expected that this compound is capable of inhibiting, reducing and/or relieving an inflammation. In this regard it has to be noted that the known application of cooling agents, although being useful in the treatment of pain and heat as clinical signs or symptoms of an inflammation, does not affect the inflammation mechanism as such, because physiological cooling substances merely interact with receptors present in the skin. The cold sensation is detected by receptors belonging to the transient receptor potential (TRP) superfamily. Migration of calcium ions through the ion channels is responsible for the changes in the perception of the temperature. As explained above, the release of inflammatory mediators is responsible for the clinical signs of an inflammation. Thus, in order to to inhibit, reduce and/or relieve skin-inflammation it is of crucial importance to reduce the release of such mediators. The most important inflammation mediators are those selected from the group consisting of TNF-α (Tumor necrosis factor-alpha), interleukins (in particular of IL-1, IL-6, IL-7, IL-8, IL-10, IL-13, IL-17, IL-18 and/or IL-31, in particular IL-1), prostaglandins (in particular $PGI_2$, $PGE_2$ and/or $PGF_{2\alpha}$) Interferon-gamma (INF-γ) and NF-κB (nuclear factor kappa-light-chain-enhancer of activated B cells. The anti-inflammatory effect of menthane carboxylic acid-N-(4-methoxyphenyl)-amide, and in particular of L-menthane carboxylic acid-N-(4-methoxyphenyl)-amide may be based (without being bound to this theory) inter alia on its characteristic of inhibiting the up-regulation of inflammatory mediators, including interleukins (in particular IL-1 and IL-6), PGE-2 (prostaglandin E2) and in particular TNF-alpha (tumor necrosis factor alpha) caused by extrinsic and intrinsic factors. It can therefore be used as an outstanding alternative or as an addition to other already well-known anti-inflammatory compounds (active substances) in cosmetic and pharmaceutical preparations or similar as an anti-inflammatory active substance Pharmaceutical Compositions The pharmaceutical compositions according to the present invention may comprise at least one additional active principle selected from the group consisting of
(A) Antitussives (cough suppressants);
(B) Expectorants;
(C) Local anaesthetics;
(D) Decongestants;
(E) Antihistamines;
(F) Analgesics;
(G) Antiseptics;
(H) Vitamins and Antibiotics
and their mixtures.

A. Antitussives

The mixture of the present invention may comprise one or more antitussives. One or more synthetic (A1) as well as one more herbal (A2) antitussives as well as mixtures consisting of one or more synthetic and one or more herbal antitussives may be included in constituent The one or more antitussives of constituent (A) of the mixture of the present invention are preferably selected from the group consisting of:

(A1) Acetyldihydrocodeine, Benzylmorphine, Codeine, Dextromethorphan, Diacetylmorphine, Dihydrocodeine, Dimemorfan, Droxypropine, Ethylmorphine, Hydrocodone, Hydromorphone, Isoaminile, Levomethadone, Levopropoxyphene, Methadone, Nicocodeine, Nicodicodeine, Normethadone, Noscapine, Pholcodine, Thebacon, Tipepidine, Zipeprol, Benzonatate, Benproperine, Bibenzonium bromide, Butamirate, Clobutinol, Clofedanol, Cloperastine, Diphenhydramine, Sodium Dibunate, Dimethoxanate, Dropropizine, Fedrilate, Glaucine, Isoaminile, Levodropropizine, Meprotixol, Morclofone, Nepinalone, Oxolamine, Oxeladin, Pentoxyverine, Pipazetate, Prenoxdiazine, Piperidione, and Theobromine, and the corresponding salts, preferably the hydrochlorides, of these compounds, and (A2) primrose root extract, extract of Iceland moss (*Cetraria islandica*), chamomile extract, extract of ribwort plantain (*Plantago lanceolata*), leaf or flower extracts of *Malva sylvestris*, and extract of Sundew (*Drosera*, preferably *D. rotundifolia, D. intermedia, D. anglica, D. ramentacea* and/or *D. Madagascariensis*, preferably an extract of roots, flowers, and/or the fruit-like capsules thereof), and their mixtures Further preferably, the one or more antitussives of constituent (A) of the mixture of the present invention (as defined above) are selected from the group consisting of primrose root extract, Iceland moss extract, chamomile extract, extract of ribwort plantain (*Plantago lanceolata*), Acetyldihydrocodeine, Benzylmorphine, Codeine, Dextromethorphan, Diacetylmorphine, Dihydrocodeine, Dimemorfan, Droxypropine, Ethylmorphine, Hydrocodone, Hydromorphone, Isoaminile, Levomethadone, Levopropoxyphene, Methadone, Nicocodeine, Nicodicodeine, Normethadone, Noscapine, Pholcodine, Thebacon, Tipepidine, Zipeprol, Benzonatate, Benproperine, Bibenzonium bromide, Butamirate, Clobutinol, Clofedanol, Cloperastine, Diphenhydramine, Sodium Dibunate, Dimethoxanate, Dropropizine, Fedrilate, Glaucine, Isoaminile, Levodropropizine, Meprotixol, Morclofone, Nepinalone, Oxolamine, Oxeladin, Pentoxyverine, Pipazetate, Prenoxdiazine, Piperidione, and Theobromine. Most preferably the one or more antitussives of constituent (A) of the mixture of the present invention (as defined above) are selected from the group consisting of Iceland moss extract, extract of ribwort plantain (*Plantago lanceolata*), Acetyldihydrocodeine, Codeine, Dextromethorphan, Dihydrocodeine, Dimemorfan, Hydrocodone, Benproperine, Clobutinol, and Pentoxyverine, and their mixtures.

B. Expectorants

Constituent (B) of the mixture of the present invention may comprise of one or more expectorants. One or more synthetic (B1) as well as one more herbal (B2) expectorants as well as mixtures consisting of one or more synthetic and one or more herbal expectorants may be included in constituent (B). The one or more expectorants of constituent (B) of the mixture of the present invention are preferably selected from the group consisting of:

(B1 Ambroxol, Bromhexine, Clenbuterol, Dembrexin, Eprazinone, Neltenexine, and the corresponding salts, preferably the hydrochlorides, of these compounds, and (B2) Guaifenesin, Levoverbenone, Tyloxapol, Acetylcysteine, Carbocysteine, Dornase alfa, Domiodol, Erdosteine, Letosteine, Mesna, Sobrerol, Stepronin, Tiopronin, ammonium chloride, antimony pentasulfide, guaiacol sulfonate, potassium iodide, camphor, thyme extract, ivy extract (preferably ivy leaf extract), cajeput oil, mountain pine oil, noble fir oil, licorice root extract, licorice juice, extract of *Radix Pimpinellae*, chestnut leaf extract (preferably of *Castanea sativa*), lavender spike oil (*Lavandula latifolia*), elderberry extract (preferably elderberry flower extract), extract of White Horehound *Marrubium vulgare*), extract of Horsetail herb (*Equisetum arvense*), flower extract of *Verbascum densiflorum*, Senega (*Polygala senega*) root extract, extract of Marshmallow (*Althaea officinalis*) (preferably leaf or root extract), And their mixtures More preferably, the one or more expectorants of constituent (B) of the mixture of the present invention are selected from the group consisting of mucolytic agents, preferably selected from the group consisting of camphor, thyme extract, ivy leaf extract, Acetylcysteine, Ambroxol, Ambroxol hydrochloride, Bromhexine, Bromhexine hydrochloride, Carbocysteine, Domiodol, Dornase alfa, Eprazinone, Eprazinone hydrochloride, Erdosteine, Letosteine, Mesna, Neltenexine, Neltenexine hydrochloride, Sobrerol, Stepronin, and Tiopronin. Most preferably the one or more expectorants of constituent (B) of the mixture of the present invention are selected from the group consisting of ivy leaf extract, Acetylcysteine, Ambroxol hydrochloride, Bromhexine, and Bromhexine hydrochloride, and their mixtures.

C. Local Anaesthetics

Optional constituent (C) of the mixture of the present invention encompass one or more local anaesthetics. It has been found that the presence of one or more local anaesthetics (C) in the mixture has the beneficial effect of soothing the pain which is one of the clinical signs or symptoms of an inflammation (see above). In this regard it has to be noted that the one more local anaesthetics (C) are not necessary to inhibit, reduce and/or relieve the inflammation since a mixture according to the invention of identical composition (with the exception that no local anaesthetic (C) is present) is also capable of inhibiting, reducing and/or relieving the inflammation.

The one or more local anaesthetics of constituent (C) of the mixture of the present invention are preferably selected from the group consisting of Benzocaine, Chloroprocaine, Cyclomethycaine, Dimethocaine, Larocaine, Piperocaine, Propoxycaine, Procaine, Novocaine, Proparacaine, Tetracaine and Amethocaine, Articaine, Bupivacaine, Cinchocaine, Dibucaine, Etidocaine, Levobupivacaine, Lidocaine, Lignocaine, Mepivacaine, Prilocalne, Ropivacaine, and Trimecaine, and the corresponding salts, preferably the hydrochlorides, of these compounds. More preferably, the one or more local anaesthetics of constituent (C) of the mixture of the present invention are selected from the group consisting of Benzocaine, Dimethocaine, Larocaine, Piperocaine, Propoxycaine, Procaine, Novocaine, Proparacaine, Cinchocaine, Dibucaine, Lidocaine, Lignocaine, Mepivacaine, and Prilocalne, or a corresponding salt, preferably a hydrochloride, of these compounds. Most preferably, the one or more local anaesthetics of constituent (C) of the mixture of the present invention are selected from the group consisting of Benzocaine, Novocaine, and Lidocaine, and the corresponding salts, preferably the hydrochlorides, of these compounds, and their mixtures.

D. Decongestants

Optional constituent (D) of the mixture of the present invention encompass one or more decongestants. It has been found that the presence of one or more decongestants (D) in the mixture has the beneficial effect of soothing and reducing the swelling which is one of the clinical signs or symptoms of an inflammation. In this regard it has to be noted that the one more decongestants (D) are not necessary to inhibit, reduce and/or relieve the inflammation since a mixture according to the invention of identical composition (with the exception that no decongestant (D) is present) is also capable of inhibiting, reducing and/or relieving the inflammation.

The one or more decongestants of constituent (D) of the mixture of the present invention are preferably selected from the group consisting of Ephedrine, Levo-methamphetamine, Naphazoline, Oxymetazoline, Phenylephrine, Phenylpropanolamine, Propylhexedrine, Pseudoephedrine, Synephrine, Tetrahydrozoline, Cafaminol, Cyclopentamine, Epinephrine, Fenoxazoline, Levonordefrin, Mephentermine, Metizoline, Norepinephrine, Tetryzoline, Tramazoline, Tuaminoheptane, Tymazoline and Xylometazoline, and the corresponding salts, preferably the hydrochlorides, of these compounds. More preferably, the one or more decongestants of constituent (D) of the mixture of the present invention (as defined above) are selected from the group consisting of Naphazoline, Oxymetazoline, Phenylephrine, Propylhexedrine, Pseudoephedrine, Tetrahydrozoline, Epinephrine, Norepinephrine, Tetryzoline, Tramazoline, Tymazoline and Xylometazoline, or a corresponding salt, preferably a hydrochloride, of these compounds. Most preferably, the one or more decongestants of constituent (D) of the mixture of the present invention (as defined above) are selected from the group consisting of Naphazoline, Oxymetazoline, Phenylephrine, Epinephrine, Tetryzoline, Tramazoline, and Xylometazoline, or a corresponding salt, preferably a hydrochloride, of these compounds, and their mixtures E. Antihistamines Optional constituent (E) of the mixture of the present invention encompass one or more antihistamines preferably one or more $H_1$ receptor antagonists. It has been found that the presence of one or more antihistamines (E) in the mixture has the beneficial effect of suppressing the histamine-induced swelling and vasodilation (flare) response. Swelling and redness (as the result of vasodiliation) belong to the clinical signs or symptoms of an inflammation. In this regard it has to be noted that the one more antihistamines (E) are not necessary to inhibit, reduce and/or relieve the inflammation since a mixture according to the invention of identical composition (with the exception that no antihistamine (E) is present) is also capable of inhibiting, reducing and/or relieving the inflammation. The one or more antihistamines of constituent (E) are preferably selected from the group consisting of Diphenhydramine, Doxylamine, Cetirizine, Loratadine, Terfenadine, Levocetirizine, Desloratadine, Fexofenadine and Triprolidine, and the corresponding salts, preferably the hydrochlorides, of these compounds. Most preferably constituent (E) comprises or consists of Triprolidine and/or Triprolidine hydrochloride, and their mixtures F. Analgesics Optional constituent (F) of the mixture of the present invention encompass one or more analgesics. It has been found that the presence of one or more analgesics (F) in the mixture has the beneficial effect of soothing the pain which is one of the clinical signs or symptoms of an inflammation. In this regard it has to be noted that the one more analgesics (F) are not necessary to inhibit, reduce and/or relieve the inflammation since a mixture according to the invention of identical composition (with the exception that no analgesic (F) is present) is also capable of inhibiting, reducing and/or relieving the inflammation. The one or more analgesics of constituent (F) are preferably selected from the group consisting of acetyl salicylic acid and its pharmaceutically acceptable salts, Diclofenac, Fenoprofen, Flurbiprofen, Tarenflurbil, Ibuprofen, Ketoprofen, Naproxen, Oxaprozin, Phenacetin and Paracetamol. Most preferably the one or more analgesics of constituent (F) are selected from the group consisting of Diclofenac, Flurbiprofen, Ibuprofen, Naproxen, Paracetamol and their mixtures G. Antiseptics Optional constituent (G) of the mixture of the present invention (as defined above) consists of one or more antiseptics, preferably selected from the group consisting of sodium chloride, ethanol, chlorhexidine, 2,4-dichlorobenzyl alcohol, amylmetacresol, hexamidine diisethionate and quaternary ammonium compounds. It has been found that the presence of one or more antiseptics (G) in the mixture has the beneficial effect of reducing the risk of infection, sepsis, or putrefaction. In this regard it has to be noted that the one more antiseptics (G) are not necessary to inhibit, reduce and/or relieve the inflammation since a mixture according to the invention of identical composition (with the exception that no antiseptic (G) is present) is also capable of inhibiting, reducing and/or relieving the inflammation. The one or more antiseptics of constituent (G) are preferably selected from the group consisting of benzalkonium chloride, cetyl trimethylammonium bromide, cetylpyridinium chloride, benzethonium chloride and dequalinium chloride. More preferably, the one or more antiseptics of constituent (G) are selected from the group consisting of sodium chloride, ethanol, chlorhexidine, 2,4-dichlorobenzyl alcohol, amylmetacresol, hexamidine diisethionate, benzalkonium chloride, cetyl trimethylammonium bromide, cetylpyridinium chloride and benzethonium chloride. Most preferably, the one or more antiseptics of constituent (G) selected from the group consisting of sodium chloride, ethanol, chlorhexidine, hexamidine diisethionate, benzalkonium chloride, cetyl trimethylammonium bromide, cetylpyridinium chloride and dequalinium chloride, and their mixtures.

H. Vitamins and Antibiotics

Optional constituent (H) of the mixture of the present invention encompass one or more vitamins (H1) or antibiotics (H2) chose from the following groups (H2) vitamin C (ascorbic acid), zinc-compounds, Dexpanthenol, calcium pantothenate, Aloe vera extract, extract of Hedge mustard (*Sisymbrium officinale*), alpha bisabolol, extract of ginger, and (H2) Tyrothricin, Fusafungine, Bacitracin, Gramicidin, Neomycin and extract of Umckaloabo (*Pelargonium sidoides*), and their mixtures.

In as far combinations of the active principles become part of the compositions of the inventions, it should be understood that it is preferred to combine those actives chosen from the sub-groups A to H which are individually preferred within said sub-groups.

The compositions may also include pharmaceutically acceptable solvents such as for example water, ethanol, ethylene glycol, glycerol and the like.

It is further preferred that the pharmaceutical compositions are essentially free of tingling sensates, preferably the mixture does not contain 2E,4E-decadienoic acid-N-isobutylamide and 2E,4E-undecadienoic acid-N-isobutylamide, more preferably the mixture is free of tingling sensates, salivating agents and/or warming sensates, because sometimes those substances have been found to enhance clinical signs or symptoms of an inflammation like pain, heat and redness.

Said pharmaceutical compositions may comprise the menthane carboxylic acid-N-(4-methoxyphenyl)-amide in amounts of about 0.0001 to about 1.0, preferably about 0.001 to about 0.1 and more preferably of about 0.01 to about 0.05% b.w.—calculated on final composition. It needs to be mentioned that the preferred concentration for said amide is by far lower than the concentration needed to achieve a cooling sensation. The compositions may comprise the amides and the secondary active principles in weight ratios of about 1:9 to about 9:1, preferably about 3:7 to about 7:3 and more preferably about 4:6 to about 6:4.

Oral Compositions

Another object of the present invention refers to an oral composition comprising (a) menthane carboxylic acid-N-(4-methoxy-phenyl)-amide,
(b) a pharmaceutically acceptable carrier, and optionally
(c) at least one additional active principle and/or
(d) at least one aroma or flavouring compound and/or
(e) at least one sweetener.

Said oral compositions can represent a final product directed to the consumer, but may also serve as an intermediate for producing a pharmaceutical composition.

Carriers

In the context of the present invention the pharmaceutical acceptable carrier (component b) can be chosen from water and aliphatic alcohols or polyols having 2 to 15 carbon atoms, including esters of said polyols. Preferably, ethanol, isopropyl alcohol or polyols, may be used as cosmetically acceptable carriers. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose and their mixtures. Also suitable are esters of acetic acid or $C_6$-$C_{22}$ fatty acids with glycerol, sch as diacetin, triacetin, and mono-, di- and/or triglycerides.

Active Principles

The oral compositions according to the present invention may comprise additional active principles (component c) selected from the group consisting of antitussives (cough suppressants), expectorants, local anaesthetics, decongestants, antihistamines analgesics, antiseptics and their mixtures. Examples for each of these sub-groups are provided above.

Aroma or Flavouring Compounds

Aroma compounds and flavouring agents (component d) are well known in the art can be added to the flavour compositions of the invention. These flavouring agents can be chosen from synthetic flavouring liquid and/or oils derived from plants leaves, flowers, fruits and so forth, and combinations thereof. Representative flavouring liquids include: artificial, natural or synthetic fruit flavours such as eucalyptus, lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derived flavours such as licorice or ginger.

The flavouring agent is preferably selected from the group consisting of essential oils and extracts, tinctures and balsams, such as, for example, anisole, basil oil, bergamot oil, bitter almond oil, camphor oil, citronella oil, lemon oil; Eucalyptus citriodora oil, eucalyptus oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the flavoured composition according to the invention comprises at least one flavouring agent, preferably two, three, four, five, six, seven, eight or more flavouring agents chosen from the following group: menthol (preferably I-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gammadecalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cisjasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

In particular preferred aroma or flavouring compounds encompass menthol, cineol, eugenol, thymol, cinnamic aldehyde, peppermint oil, spearmint oil, eucalyptus oil, thyme oil, cinnamon oil, clove oil, spruce needle oil, fennel oil, sage oil, aniseed oil, star anise oil, chamomile oil, and caraway oil, and their mixtures.

Sweeteners

Suitable sweet-tasting substances, including natural sources of these substances (component e), such as for example sweet-tasting carbohydrates or sugars (e.g. sucrose (synonymous with saccharose), trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin) or vegetable preparations containing predominantly these carbohydrates (e.g. from sugar beet (Beta vulgaris ssp., sugar fractions, sugar syrup, molasses), from sugar cane (Saccharum officinarum ssp., e.g. molasses, sugar syrups), from sugar maple (Acer ssp.), from agave (agave thick juice), synthetic/enzymatic hydrolysates of starch or sucrose (e.g. invert sugar syrup, highly enriched fructose syrups made from corn starch), fruit concentrates (e.g. from apples or pears, apple syrup, pear syrup), sugar alcohols (e.g. erythritol, threitol, arabitol, ribitol, xylitol, sorbitol, mannitol, dulcitol, lactitol), proteins (e.g. miraculin, monellin, thaumatin, curculin, brazzein), sweeteners (magap, sodiumcyclamate, acesulfame K, neohesperidin dihydrochalcone, saccharin sodium salt, Aspartame®, superaspartame, neotame, alitame, sucralose, stevioside, rebaudioside, lugduname, carrelame, sucrononate, sucrooctate, monatin, phyllodulcin), certain sweet-tasting amino acids (glycine, D-leucine, D-threonine, D-asparagine, D-phenylalanine, D-tryptophan, L-proline), other sweet-tasting low-molecular substances (e.g. hernandulcin, dihydrochalcone glycosides, glycyrrhizin, glycyrrhetinic acid ammonium salt or other glycyrrhetinic acid derivatives), liquorice extracts (Glycyrrhizza glabra ssp.), Lippia dulcis extracts, Momordica ssp. extracts or individual substances (in particular Momordica grosvenori [Luo Han Guo] and the mogrosides obtained therefrom), Hydrangea dulcis or Stevia ssp. (e.g. Stevia rebaudiana) extracts or individual substances.

Physical Appearance of the Compositions

The pharmaceutical compositions according to the represent invention may represent solutions, emulsions, oral rinses, sprays, syrups, tablets, capsules, granules, pellets, films or confectioneries as for example hard candies, soft candies, throat lozenges, cough lozenges, medicinal pastilles, throat discs, film strips, chewable tablets, effervescent tablets, throat sprays, nasal sprays, nasal drops or cough syrups. In as far oral compositions are concerned these embodiments may also represent tooth pastes, mouthwashes or chewing gums.

A pharmaceutical or an oral compositon, in particular the liquid or solid form as described above can furthermore be processed by encapsulation in order to obtain either macro- or microcapsules—

To obtain macro-capsules the compositions are typically encapsulated with a solid shell material, which is preferably chosen from starches, degraded or chemically or physically modified starches (in particular dextrins and maltodextrins), gelatines, wax materials, liposomes, gum arabic, agar-agar, ghatti gum, gellan gum, modified and non-modified celluloses, pullulan, curdlan, carrageenans, algic acid, alginates, pectin, inulin, xanthan gum and mixtures of two or more of said substances. The solid shell material is preferably selected from gelatine (pork, beef, poultry and/or fish gelatines or mixtures thereof, preferably including at least one gelatine having a Bloom value of greater than or equal to 200, preferably having a Bloom value of greater than or equal to 240), maltodextrin (preferably obtained from maize, wheat, tapioca or potato, preferred maltodextrins displaying a DE value in the range from 10 to 20), modified cellulose (e.g. cellulose ether), alginates (e.g. Na alginate), carrageenan (beta-, iota-, lambda- and/or kappa-carrageenan), gum arabic, curdlan and/or agar-agar. Gelatine is used in particular because of its good availability in various Bloom values. Particularly preferred for oral hygiene purposes are seamless gelatine or alginate capsules, whose shell dissolve very quickly in the mouth or bursts when chewed, thus releasing the active ingredient in the oral cavity. Production can take place as described for example in EP 0389700 A, U.S. Pat. Nos. 4,251,195, 6,214,376, WO 2003 055587 A1 or WO 2004 050069 A1.

On the other hand, the term "microcapsule" is understood describing a spherical aggregate with a diameter of about 0.1 to about 5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers, such as polyacrylates, polyamides, polyvinyl alcohol or polyvinyl pyrrolidone. Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicetin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids).

According to an alternative, preferred embodiment, a pharmaceutical product or an oral a flavoured composition according to the invention, optionally with further constituents of the preparation according to the invention, into emulsions, into liposomes, for example starting from phosphatidyl choline, into microspheres, into nanospheres or also into capsules, granules or extrudates prepared from a matrix (carrier) suitable for pharmaceutical products, for example prepared from starch, starch derivatives (for example modified starch), cellulose or cellulose derivatives (for example hydroxypropylcellulose), other polysaccharides (for example dextrin, alginate, curdlan, carageenan, chitin, chitosan, pullulan), natural fats, natural waxes (for example beeswax, carnauba wax), prepared from proteins, for example gelatin or other natural products (for example shellac) or non-natural matrix materials (such as polyurea). In said embodiment, depending on the matrix, the products may be treated by spray drying, spray granulation, melt granulation, coacervation, coagulation, extrusion, melt extrusion, emulsion methods, coating or other suitable encapsulation methods and optionally a suitable combination of the above-stated methods.

INDUSTRIAL APPLICATION

A final object of the present invention is directed to a non-therapeutic method for treating and/or preventing inflammations of the respiratory tract wherein a working amount of menthane carboxylic acid-N-(4-methoxy-phenyl)-amide in a pharmaceutical acceptable solvent is administered orally. More particularly, the amide can be used for the treatment of coughs, colds, oral, nasal, throat or pharyngeal inflammation, sore throat, hoarseness and other inflammations of the respiratory tract.

EXAMPLES

Examples 1 to 3

Anti-inflammatory Effect

In the course of cutaneous inflammations, leukocytes, such as, for example, the polymorphonuclear neutrophilic granulocytes (PMN), are stimulated by peptides, such as, for example, cytokines, to emit messenger substances, such as, for example, leucotriene, which are released from activated or necrotic cells in the dermis. These activated PMNs release not only proinflammatory cytokins, leucotrienes and proteases, but also ROS, such as, for example, superoxides and hypochlorite anions, which have the task of destroying pathogenic microbes or fungi which have penetrated it. This activity of the PMNs during inflammation is known as respiratory burst and can lead to additional tissue damage. To investigate to what extent the amide is able to prevent or reduce respiratory burst, a cell line of human leucemic granulocytes of these PMNS was incubated together with the test substances at 37° C. from 5% by volume of $CO_2$. After the respiratory burst had been triggered by adding a yeast extract (zymosan) to the cell solution, the release of superoxide anions was determined by means of their reaction with Luminol. The results are summarized in Table 1. The values given are the cell numbers and the amount of released ROS in relative percentages compared with the standard as an average value of a measurement series with triplicate determination.

TABLE 1

| | | Respiratory burst | | |
|---|---|---|---|---|
| Ex. | Active | Concentration % b.w. | Cell numbers | Released ROS |
| 0 | None | | 100 | 100 |
| 1 | Menthane carboxylic | 0.001 | 104 ± 1 | 37 ± 25 |
| 2 | acid-N-(4-methoxy- | 0.01 | 94 ± 3 | 9 ± 4 |
| 3 | phenyl)-amide | 0.1 | 93 ± 1 | 8 ± 4 |

The results from Table 1 clearly show that menthane carboxylic acid-N-(4-methoxyphenyl) amide has a strong inhibiting effect on the respiratory burst of human granulocytes without damaging the granulocytes.

The following Tables 2 to 6 show various formulations for oral compositions comprising a working amount of menthane carboxylic acid-N-(4-methoxyphenyl) amide

TABLE 1

Composition cough syrup

| Component | Conc. [% b.w.] |
|---|---|
| Sorbit | 34.0 |
| Xanthan gum | 0.7 |
| Citric acid | 0.3 |
| Potassium sorbate | 0.1 |
| Anise aroma | 0.02 |
| Menthane carboxylic acid-N-(4-methoxy-phenyl)-amide | 0.01 |
| Water | Ad 100 |

TABLE 2

Composition hard candy against cough

| Component | Conc. [% b.w.] |
|---|---|
| Saccharose | 60.0 |
| Glucose syrup | 30.0 |
| Menthol | 0.5 |
| Spearmint oil | 0.5 |
| Menthane carboxylic acid-N-(4-methoxy-phenyl)-amide | 0.01 |
| Dye (caramel) | 0.3 |
| Water | Ad 100 |

TABLE 3

Composition throat spray

| Component | Conc. [% b.w.] |
|---|---|
| 2,3 Dichlorbenzyl alcohol | 0.7 |
| Amyl metacresol | 0.1 |

TABLE 3-continued

Composition throat spray

| Component | Conc. [% b.w.] |
|---|---|
| Levomenthol | 0.1 |
| Menthane carboxylic acid-N-(4-methoxy-phenyl)-amide | 0.01 |
| Spearmint oil | 0.3 |
| Ethanol | 20.0 |
| Propylene glycol | 10.0 |
| Water | Ad 100 |

TABLE 4

Composition tooth paste

| Component | Trade name | Conc. [% b.w.] |
|---|---|---|
| Precipitated silica | Sident ® 12 DS | 18.0 |
| Silica gel | Aerosil ® 200 | 0.8 |
| Sorbit | | 17.5 |
| Glycerol | | 17.5 |
| Carboxy methyl cellulose | Relatin ® 100 SR | 0.9 |
| Sodium lauryl sulfate | Texapon ® K1296 | 2.0 |
| Sodium fluoride | | 0.22 |
| Saccharin sodium | | 0.2 |
| Menthane carboxylic acid-N-(4-methoxy-phenyl)-amide | | 0.01 |
| Water | | Ad 100 |

TABLE 5

Composition mouthwash

| Component | Trade name | Conc. [% b.w.] |
|---|---|---|
| Ethanol (96% b.w.) | | 10.0 |
| Sorbitan monolaurate + 20EO | Tween ® 20 | 0.4 |
| Menthane carboxylic acid-N-(4-methoxy-phenyl)-amide | | 0.01 |
| Sorbit (70% b.w. aqueous solution) | | 8.0 |
| p-Hydroxybenzoic acid methyl ester | | 0.2 |
| Water | | Ad 100 |

TABLE 6

Compositions for chewing gums

| Composition | A | B | C | D | E | F | G | H |
|---|---|---|---|---|---|---|---|---|
| Polyisobutylene (MW 20.000) | 30.0 | 30.0 | 30.0 | 40.0 | 20.0 | 20.0 | 25.0 | 30.0 |
| Glucose | 51.0 | 51.0 | 51.0 | 42.5 | | | | |
| Corn syrup | 10.0 | 10.0 | 10.0 | 8.0 | | | | |
| Sorbitol | | | | | 51.0 | 51.0 | 47.5 | 44.5 |
| Mannitol | | | | | 5.0 | 5.0 | 4.3 | 3.6 |
| Glycerol | 1.8 | 1.8 | 1.8 | 1.8 | 8.0 | 8.0 | 8.0 | 7.0 |
| Lycasin:Glycerol (1:1) | | | | | 8.2 | 8.2 | 8.0 | 7.0 |
| Lecithine | | | | | 0.2 | 0.2 | 0.2 | 0.2 |
| Menthane carboxylic acid-N-(4-methoxy-phenyl)-amide | 0.01 | 0.01 | 0.01 | 0.01 | 0.01 | 0.01 | 0.01 | 0.01 |
| Spearmint aroma | 0.01 | 0.01 | 0.01 | 0.01 | 0.01 | 0.01 | 0.01 | 0.01 |
| Water | | | | Ad 100 | | | | |

The invention claimed is:

1. A method for treating coughs, colds, oral, nasal throat or pharyngeal inflammation, sore throat, hoarseness and other inflammations of the respiratory tract said method comprising orally administering to a subject in need thereof a composition comprising a concentration of menthane carboxylic acid-N-(4-methoxy-phenyl)-amide in the range from 0.0001 to 0.1% by weight,
   wherein respiratory burst of human granulocytes is inhibited without damaging granulocytes, and
   wherein inflammation is reduced or inhibited.

2. The method according to claim 1, wherein release of TNF-$\alpha$ (Tumor necrosis factor-alpha) is reduced.

3. The method according to claim 1, wherein release of an interleukin is reduced.

4. The method according to claim 1, wherein release of a prostaglandin is reduced.

5. The method according to claim 1, wherein release of interferon-gamma (INF-$\gamma$) and/or NF-$\kappa$B (nuclear factor kappa-light-chain-enhancer of activated B cells) is reduced.

6. The method according to claim 1, wherein said composition further comprises an additional active principle selected from the group consisting of antitussives (cough suppressants), expectorants, local anaesthetics, decongestants, antihistamines analgesics, antiseptics and mixtures thereof.

7. The method according to claim 1 wherein the menthane carboxylic acid-N-(4-methoxy-phenyl)-amide is orally administered in a pharmaceutical acceptable solvent.

8. The method according to claim 1 wherein the menthane carboxylic acid-N-(4-methoxy-phenyl)-amide is the only active ingredient administered.

* * * * *